(12) United States Patent
Goyal

(10) Patent No.: US 7,367,214 B2
(45) Date of Patent: May 6, 2008

(54) SHOCK AND LAUNCH APPARATUS

(75) Inventor: Suresh Goyal, Warren, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 170 days.

(21) Appl. No.: 11/434,647

(22) Filed: May 16, 2006

(65) Prior Publication Data

US 2007/0266764 A1     Nov. 22, 2007

(51) Int. Cl.
*G01M 7/00*     (2006.01)
(52) U.S. Cl. .................................... 73/12.09
(58) Field of Classification Search ................ 73/12.09
See application file for complete search history.

(56) References Cited

U.S. PATENT DOCUMENTS

| | | | |
|---|---|---|---|
| 4,023,396 | A | 5/1977 | Yakshin et al. |
| 4,426,683 | A | 1/1984 | Kissell |
| 4,433,570 | A | 2/1984 | Brown et al. |
| 4,980,526 | A | 12/1990 | Reneau |
| 5,000,030 | A | 3/1991 | Umeda et al. |
| 5,355,716 | A | 10/1994 | Castelli |
| 5,450,742 | A | 9/1995 | Baltz et al. |
| 5,483,845 | A * | 1/1996 | Stein et al. ................ 73/865.3 |
| 5,623,094 | A * | 4/1997 | Song et al. ................ 73/12.07 |
| 6,308,555 | B1 | 10/2001 | Liem et al. |
| 6,374,661 | B1 | 4/2002 | Buratynski et al. |
| 6,443,013 | B1 | 9/2002 | Smith et al. |

OTHER PUBLICATIONS

S. Goyal et al., "Shock Protection of Portable Electronic Products: Shock Response Spectrum, Damage Boundary Approach, and Beyond," Shock and Vibration, vol. 4, No. 3, pp. 169-191 (1997).
S. Goyal et al., "The Dynamics of Clattering I: Equation of Motion and Examples," J. of Dynamic Systems, Measurement, and Control, Mar. 1998, vol. 120, pp. 83-93.
S. Goyal et al., "The Dynamics of Clattering II: Global Results and Shock Protection," J. of Dynamic Systems, Measurement, and Control, vol. 120, Mar. 1998, pp. 94-102.
S. Goyal et al., "Simulation of Dynamics of Interacting Rigid Bodies Including Friction II: Software System Design and Implementation," Engineering with Computers (1994) 10, pp. 175-195.

* cited by examiner

*Primary Examiner*—Max Noori

(57) ABSTRACT

One embodiment of a shock and launch apparatus comprises a first carriage and a second carriage adapted to move along a carriage guide, wherein the first carriage has a mass $M_1$ greater than a mass $M_2$ of the second carriage; the carriage guide, associated with a substantially linear path of movement of the first and second carriages; and a carriage stop, capable of being positioned at a first position and a second position, wherein the carriage stop in the first position is at least partially in the path of movement of the second carriage. In one embodiment, the carriage stop in the second position is not in the path of movement of the second carriage. One embodiment of a method comprises providing a velocity-reversing impact to the first carriage; providing a plurality of velocity-amplifying impacts between the second carriage and the first carriage after the velocity-reversing impact to the first carriage, providing a plurality of velocity-reversing impacts between the second carriage and the carriage stop in the first position; and changing the position of the carriage stop to the second position.

20 Claims, 9 Drawing Sheets

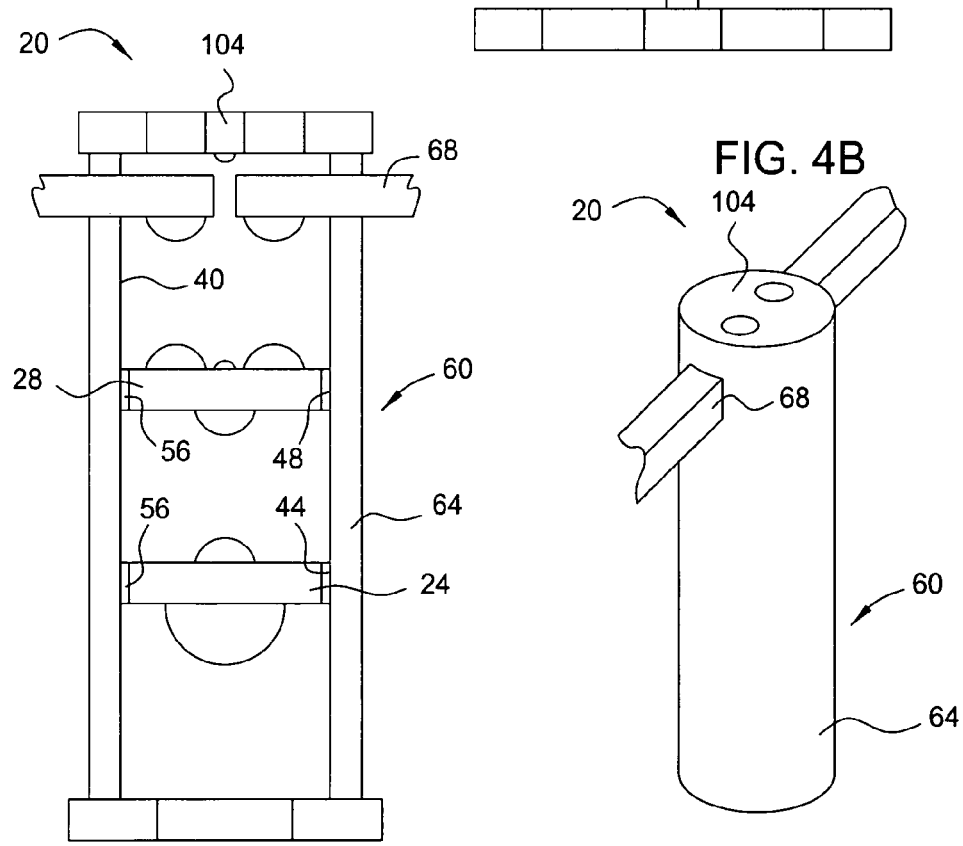

SHOCK AND LAUNCH APPARATUS

CROSS REFERENCE TO RELATED APPLICATIONS

This application is related to U.S. patent application Ser. No. 11/378,019, entitled "Shock Apparatus," filed Mar. 17, 2006, which is hereby incorporated by reference in its entirety.

This application is also related to U.S. patent application Ser. No. 11/378,082, entitled "Rotational and Linear Shock Apparatus," filed Mar. 17, 2006, which is hereby incorporated by reference in its entirety.

BACKGROUND OF THE INVENTION

1. Field of the Invention

The present invention generally relates to mechanical shock and to launching objects, and more particularly to apparatuses and methods for providing a mechanical shock and for launching an object.

2. Description of the Related Art

Many types of devices and structures require the ability to withstand a certain level of acceleration applied over a certain time period, i.e., a shock acceleration. Examples of such devices include micro-electro-mechanical systems (MEMs), nanodevices, photonic devices, and RF devices. Some apparatuses and methods used to deliver shock accelerations include drop testing, i.e., dropping a test object from a predetermined height; and ballistic testing, i.e., attaching the test object to a ballistic projectile which is launched by a cannon. A Split Hopkinson Bar may also be used. Such apparatuses and methods have practical limitations. For example, drop testing is limited by the height from which an object may be dropped, which in turn limits the magnitude of acceleration that may be produced. Also, ballistic methods may be undesirably dangerous and expensive.

Also, many objects need to be accelerated to a certain velocity. Examples of such objects include satellites, some types of vehicles, and ammunition. Some apparatuses and methods used to accelerate objects to a velocity include ballistic methods and attaching the test object to a rocket. One limitation of such methods is that may be undesirably dangerous and expensive.

SUMMARY OF THE INVENTION

Various deficiencies of the prior art are addressed by the present invention, one embodiment of which is a shock and launch apparatus. One embodiment of the shock and launch apparatus comprises a first carriage and a second carriage adapted to move along a carriage guide, wherein the first carriage has a mass $M_1$ greater than a mass $M_2$ of the second carriage; the carriage guide, associated with a substantially linear path of movement of the first and second carriages; and a carriage stop, capable of being positioned at a first position and a second position, wherein the carriage stop in the first position is at least partially in the path of movement of the second carriage. In one embodiment, the carriage stop in the second position is not in the path of movement of the second carriage.

One embodiment of a method comprises providing a velocity-reversing impact to the first carriage; providing a plurality of velocity-amplifying impacts between the second carriage and the first carriage after the velocity-reversing impact to the first carriage, wherein the first carriage has the mass $M_1$ greater than the mass $M_2$ of the second carriage; providing the plurality of velocity-reversing impacts between the second carriage and the carriage stop in the first position; and changing the position of the carriage stop to the second position.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3 depicts a sectional view of an embodiment of the shock and launch apparatus having a single carriage guide rod.

FIG. 4a depicts a sectional view of an embodiment of the shock and launch apparatus having a carriage guide comprising an enclosing structure.

FIG. 4b depicts a perspective view of the embodiment of the shock and launch apparatus depicted in FIG. 4a.

To facilitate understanding, identical reference numerals have been used, where possible, to designate identical elements that are common to the figures.

DETAILED DESCRIPTION

Figure 1:
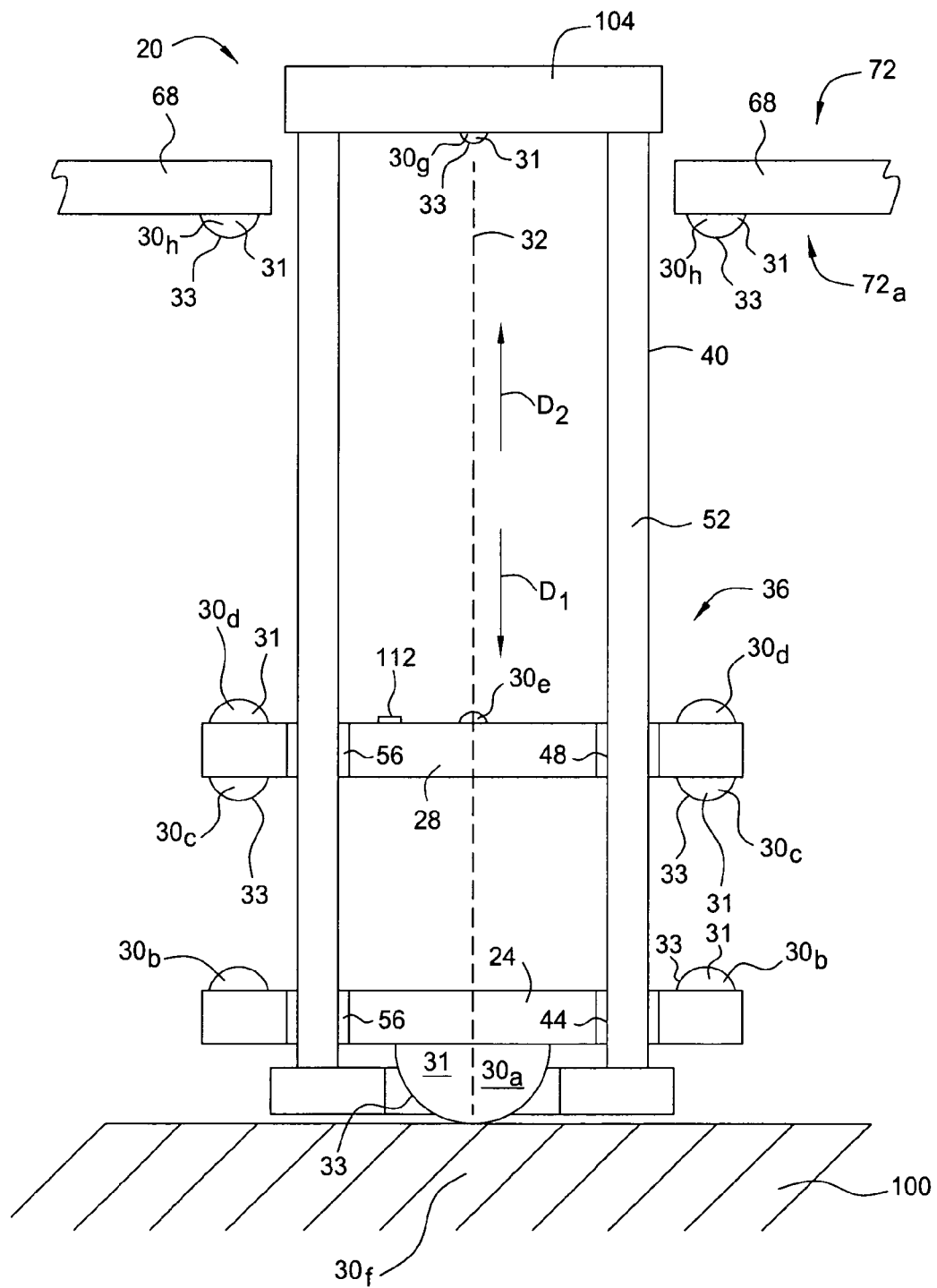
FIG. 1 depicts a sectional view of an embodiment of a shock and launch apparatus according to the present invention, the depicted embodiment capable of providing a shock acceleration.
Figure 2:
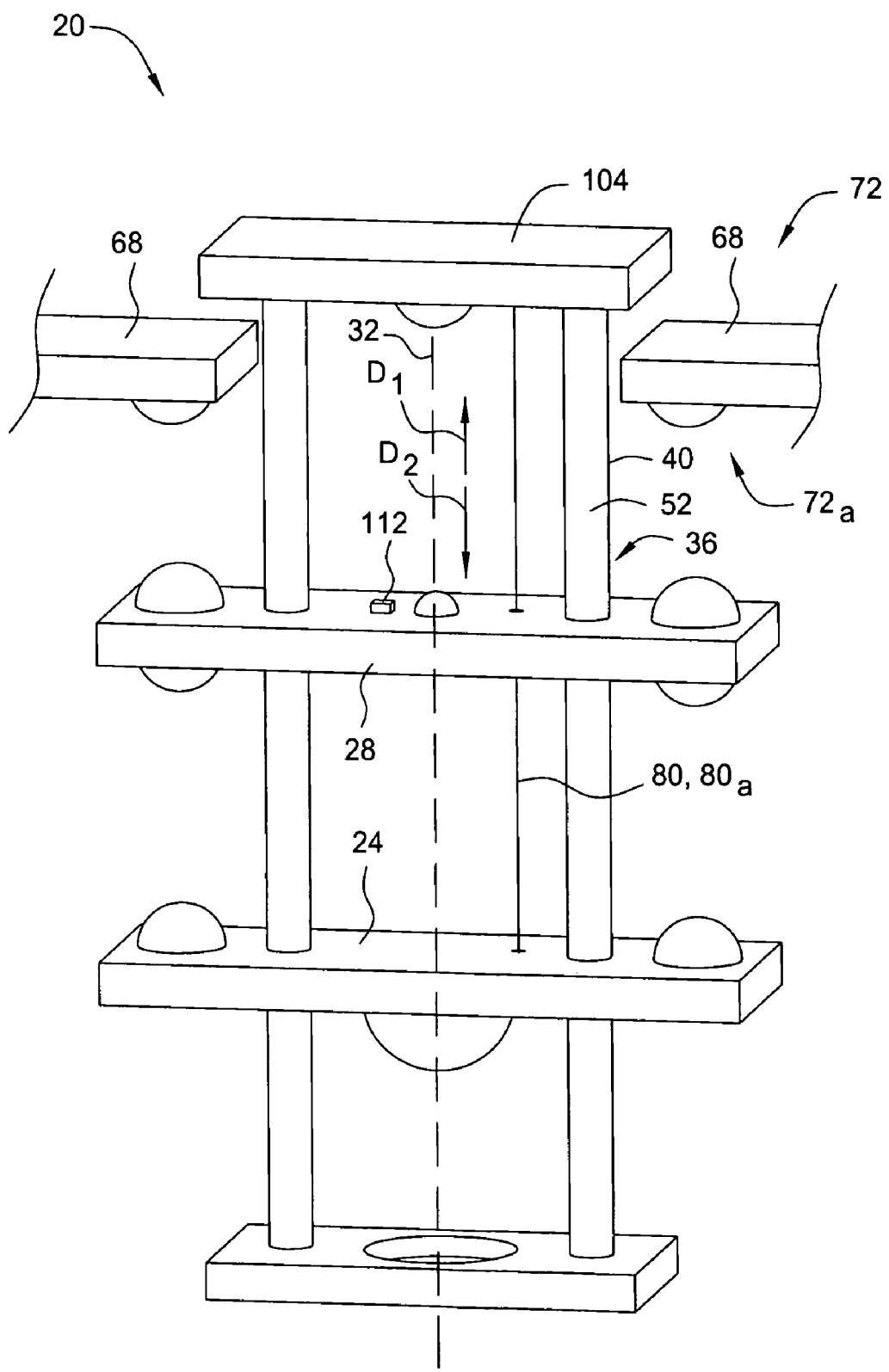
FIG. 2 depicts a perspective view of the embodiment of the shock and launch apparatus depicted in FIG. 1.

FIG. 1 depicts a sectional view of one embodiment of a shock and launch apparatus 20 according to the present invention, and FIG. 2 depicts a perspective view of the embodiment of the shock and launch apparatus 20 depicted in FIG. 1.

The shock and launch apparatus 20 comprises a first carriage 24 and a second carriage 28 capable of moving along a substantially linear path 32 and impacting each other. The first carriage 24 has a first mass $M_1$ and the second carriage 28 has a second mass $M_2$. The first mass $M_1$ is greater than the second mass $M_2$. The first and second carriages 24, 28 are spatially ordered along the path 32. The spatial ordering is relative to each other and to other components of the shock and launch apparatus 20, and is according to the relative masses of the first and second carriages 24, 28.

The shock and launch apparatus 20 comprises a carriage guide 36 to guide the movement of the first and second carriages 24, 28 along the path 32. The carriage guide 36 is also capable of maintaining the relative spatial ordering of the first and second carriages 24, 28 during operation of the shock and launch apparatus 20.

The first and second carriages 24, 28 and the carriage guide 36 are adapted to provide movement of the first and second carriages 24, 28 along the carriage guide 36. In one embodiment, the carriage guide 36 comprises a surface 40 which contacts a surface 44 of the first carriage 24 and a surface 48 of the second carriage 28. The surfaces 44, 48 of the first and second carriages 24, 28 move along the surface 40 of the carriage guide 36. For example, in one embodiment, the carriage guide 36 comprises at least one guide rod 52, and the first and second carriages 24, 28 move along the path 32 by sliding along the guide rod 52. In the embodiment depicted in FIG. 1, the carriage guide 36 comprises a pair of guide rods 52. FIG. 3 depicts an embodiment of the shock and launch apparatus 20 comprising a carriage guide 36 having a single guide rod 52.

In one embodiment, the surfaces 44, 48 of the first and second carriages 24, 28 which contact the surface 40 of the carriage guide 36 provide a relatively low friction interaction with the surface 40 of the carriage guide 36. For example, in one embodiment, the first and second carriages 24, 28 each comprise at least one bearing 56 which has the surface 44, 48. In the embodiment depicted in FIG. 1, the first and second carriages 24, 28 each comprise a pair of linear bearings 56 which facilitate the movement of the first and second carriages 24, 28 along the guide rods 52.

Other embodiments of the carriage guide 36 also exist. In one embodiment, the carriage guide 36 comprises a structure 60 which at least partially encloses the first and second carriages 24, 28. For example, FIG. 4a depicts a sectional view of an embodiment of the shock and launch apparatus 20 in which the carriage guide 36 comprises a hollow cylinder 64 which completely encloses the first and second carriages 24, 28. FIG. 4b depicts a perspective view of the embodiment of the shock and launch apparatus 20 depicted in FIG. 4a. In still other embodiments, the carriage guide 36 comprises a means to guide the first and second carriages 24, 28 without contacting the first and second carriages 24, 28 at least part of the time. For example, the carriage guide 36 may comprise a means to generate an electromagnetic field which interacts with the first and second carriages 24, 28 to exert a force on the first and second carriages 24, 28 to guide them. Optionally, the carriage guide 36 comprises other means to exert a force to guide the first and second carriages 24, 28 such as, for example, a means to generate a pressurized gas or liquid which may be applied to the first and second carriages 24, 28.

The shock and launch apparatus 20 comprises a carriage stop 68 capable of selectively interacting with the movement of the second carriage 28. The carriage stop 68 has a first state 72 in which it interacts with the movement of the second carriage 28 in a first manner to provide a velocity-reversing change of movement of the second carriage 28. The carriage stop also has a second state 76 in which it either interacts with the movement of the second carriage 28 in a second manner or does not interact with the movement of the second carriage 28.

In one embodiment, the carriage stop 68 is a selectively positionable carriage stop 68. In this embodiment, the first state 72 of the carriage stop 68 is a first position 72a of the carriage stop 68 and the second state 76 is a second position 76a (or 76b) of the carriage stop 68. In the embodiment depicted in FIG. 1, the carriage stop 68 is a selectively positionable carriage stop 68.

Figure 5A:
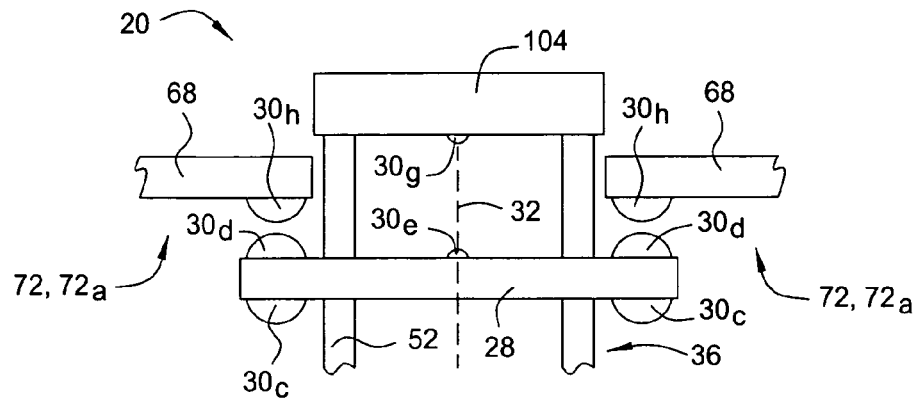
FIGS. 5a-b depict an embodiment of the shock and launch apparatus having a carriage stop in one embodiment of a first position in FIG. 5a and in one embodiment of a second position in FIG. 5b.

FIG. 5a depicts one embodiment of the first position 72a of the selectively positionable carriage stop 68. The first position 72a of the carriage stop 68 is at least partially in the path 32 of movement of the second carriage 28. The interaction between the carriage stop 68 in the first position 72a and the second carriage 28 comprises an impact between the carriage stop 68 and the second carriage 28. The carriage stop 68 in the first position 72a is a barrier to the movement of the second carriage 28 and provides a velocity-reversing impact to the second carriage 28.

Figure 5B:
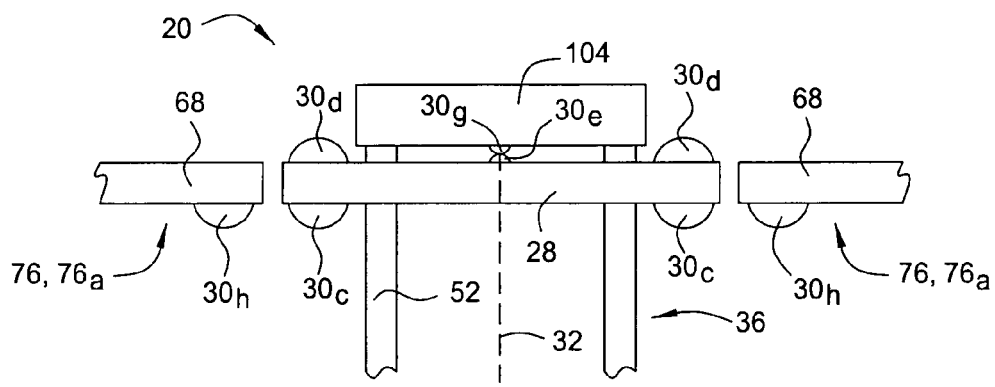

FIG. 5b depicts one embodiment of the second position 76a of the selectively positionable carriage stop 68. In the embodiment depicted in FIG. 5b, in the second position 76a no portion of the carriage stop 68 is in the path 32 of movement of the second carriage 28.

Figure 5C:
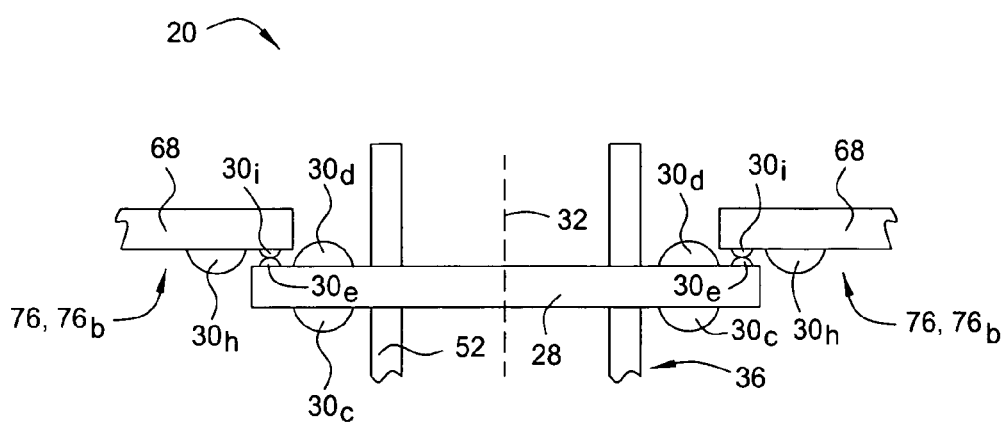
FIG. 5c depicts an embodiment of the shock and launch apparatus having an embodiment of the carriage stop in another embodiment of the second position.

FIG. 5c depicts another embodiment of the second position 76b of the selectively positionable carriage stop 68. In the embodiment depicted in FIG. 5c, in the second position 76b the carriage stop 68 is at least partially in the path 32 of movement of the second carriage 28, but interacts with the second carriage 28 in a different manner than the carriage stop 68 in the first position 72a.

In one embodiment, the first position 72a of the carriage stop 68 is a stationary position. In another embodiment, the first position 72a of the carriage stop is a non-stationary position, i.e. the carriage stop is moving while it is in the first position 72a.

Figure 6:
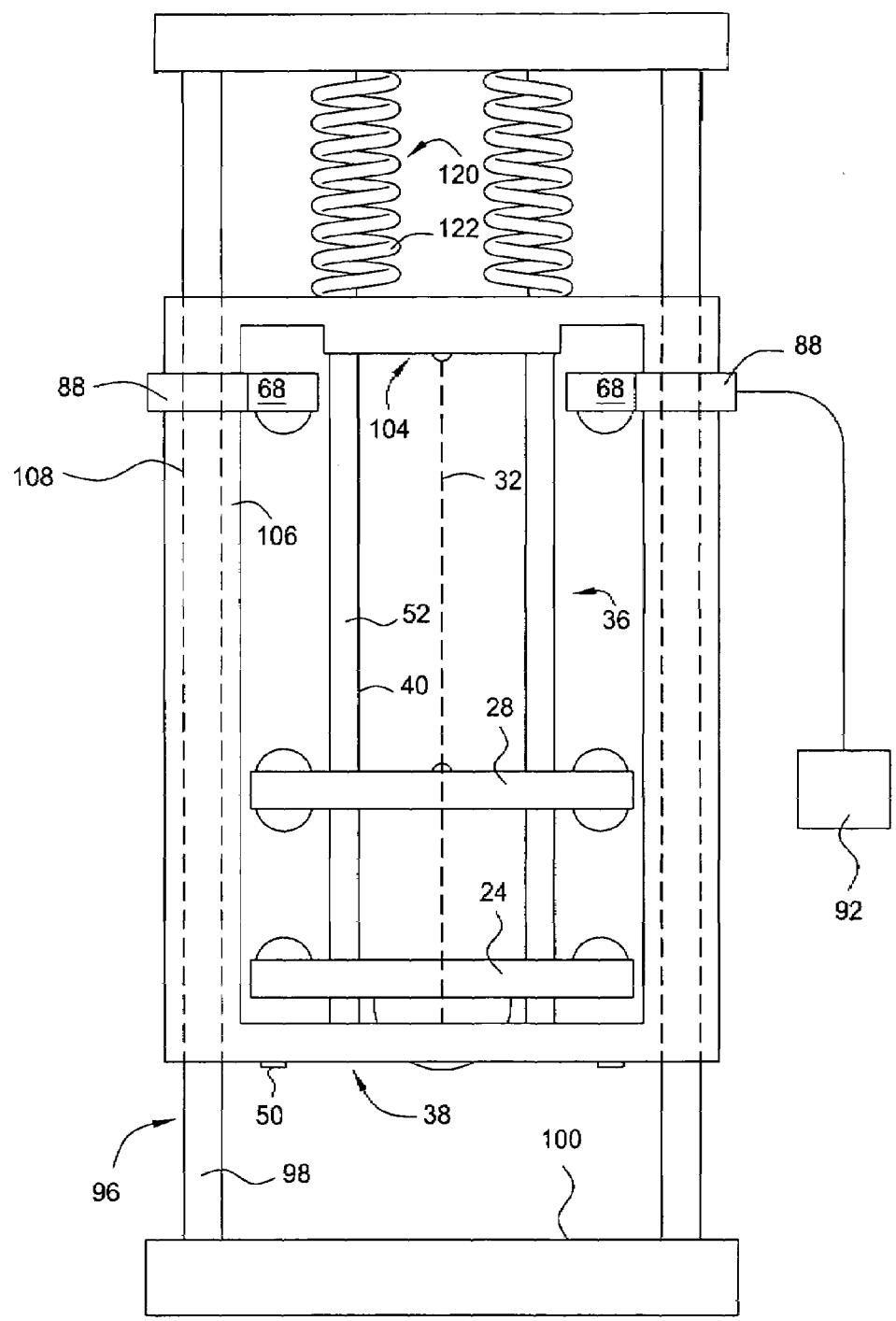
FIG. 6 depicts an embodiment of the shock and launch apparatus comprising an apparatus guide.

The shock and launch apparatus 20 comprises a means for switching 88 between the first and second states 72, 76 of the carriage stop 68; e.g., a switch apparatus 88. In one embodiment, the means for switching 88 is responsive to at least one of: the position of the first carriage 24, the velocity of the first carriage 24, the velocity of the second carriage 28, the number of impacts that have occurred between the first and second carriages 24, 28, or the number of impacts that have occurred between the second carriage 28 and the carriage stop 68 in the first state 72. In one embodiment, the means for switching 88 comprises a means for physically moving at least part of the carriage stop 68 between the first state 72 and the second state 76. Embodiments of the means for switching 88 can move the carriage stop 68 in various ways, including rotating or linearly translating the carriage stop 68. Optionally, the means for switching 88 comprises at least one of: an electric motor or a pneumatic actuator. FIG. 6 depicts one embodiment of the shock and launch 20 apparatus comprising the means for switching 88.

In one embodiment, the shock and launch apparatus 20 comprises a means for detecting 92 the at least one of: the position of the first carriage 24, the velocity of the first carriage 24, the velocity of the second carriage 28, the number of impacts that have occurred between the first and second carriages 24, 28, or the number of impacts that have occurred between the second carriage 28 and the carriage stop 68 in the first state 72. Detecting the velocity of the first or second carriages 24, 28 includes detecting at least one of: the velocity magnitude or the velocity direction. In one embodiment, the means for detecting 92 comprises a detector 92. Optionally, the means for detecting 92 comprises at least one of: an optical sensor or an accelerometer.

In one embodiment, the shock and launch apparatus 20 comprises a first target 100 capable of impacting the first carriage 24. Optionally, however, the first target 100 is part of an apparatus or environment other than the shock and launch apparatus 20. In one embodiment, the first target 100 is a fixed-position object such as, e.g., the ground, a fixture, a table-top, or other non-moving surface. In another embodiment, the first target 100 is a moving object or an object which moves at least part of the time. For example, in one embodiment the first target 100 comprises a plate that is selectively actuated to move upwards towards the first carriage 24.

In one embodiment, the shock and launch apparatus 20 comprises a second target 104 capable of impacting the second carriage 28.

Variation of the shape, size and weight of the first and second carriages 24, 28 is possible. The first and second carriages 24, 28 each comprise at least one impact portion 30 which is the portion 30 where an impact with another object, for example the first or second carriage 24, 28 or the first or second targets 100, 104, takes place. In one embodiment, the first and second carriages 24, 28 each comprise a plurality of impact portions 30, with selected subsets of the plurality of impact portions 30 of each of the first and second carriages 24, 28 being adapted differently. In one embodiment, the first carriage 24 comprises at least one impact portion 30a where an impact with the first target 100 occurs, and at least one impact portion 30b where an impact with the second carriage 28 occurs. In one embodiment, the second carriage comprises at least one impact portion 30c where an impact with the first carriage occurs, at least one impact portion 30d where an impact with the carriage stop 68 in the first state 72 occurs, and at least one impact portion 30e where an impact with either the second target 104 or the carriage stop 68 in one embodiment of the second state 76b occurs.

Variation of the shape, size and weight of the first and second targets 100, 104 is also possible. The first target 100 comprises at least one impact portion 30f where an impact with the first carriage 24 takes place. In one embodiment, the second target comprises an impact portion 30g where an impact with the second carriage 28 takes place.

The carriage stop 68 also comprises at least one impact portion 30. For example, the carriage stop in the first state 72 comprises an impact portion 30h where an impact with the second carriage 28 occurs. In one embodiment, the carriage stop in one embodiment of the second state 76b comprises an impact portion 30i where an impact with the impact portion 30e of the second carriage 28 occurs.

Figure 5D:
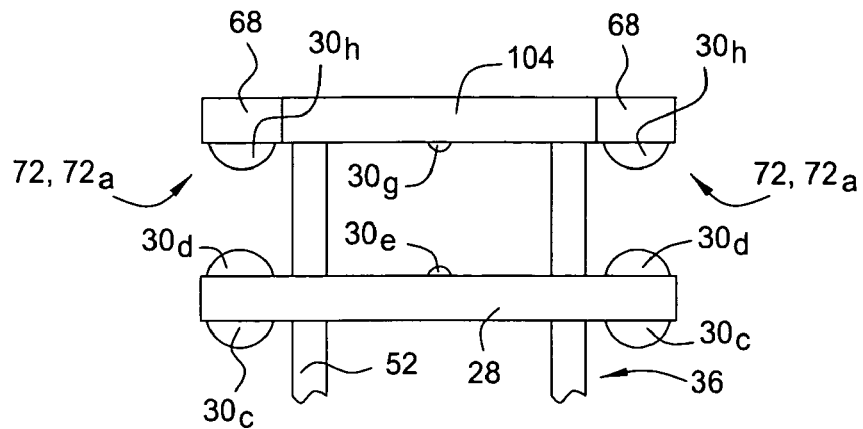
FIG. 5d depicts an embodiment of the shock and launch apparatus having an embodiment of the carriage stop which is connected to an embodiment of a second target, the carriage stop being in an embodiment of the first position.
Figure 5E:
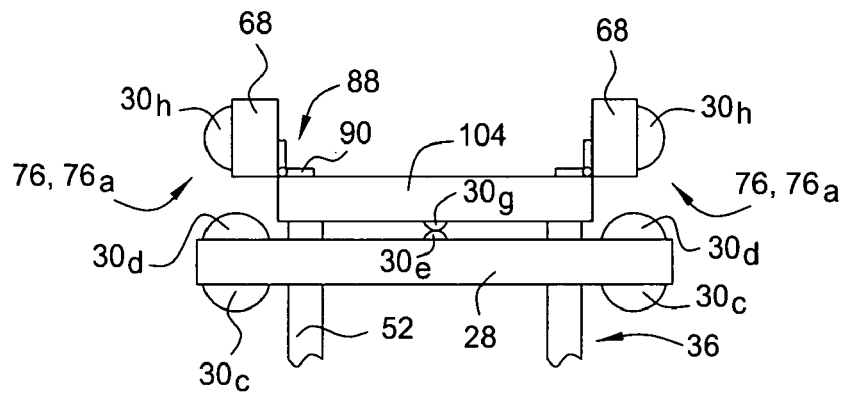
FIG. 5e depicts an embodiment of the shock and launch apparatus having an embodiment of the connected carriage stop in an embodiment of the second position.
Figure 5F:
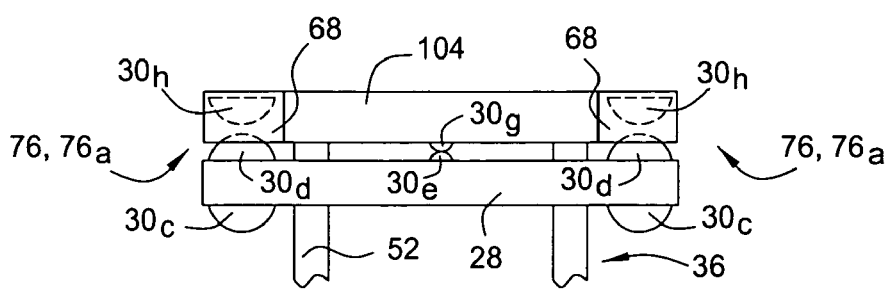
FIG. 5f depicts an embodiment of the shock and launch apparatus having another embodiment of the connected carriage stop in an embodiment of the second position.

In one embodiment, the carriage stop 68 may be connected to the second target 104. Connecting the carriage stop 68 to the second target 104 optionally includes the carriage stop 68 being integral to the second target 104. For example, FIGS. 5d-f depict embodiments of the shock and launch apparatus 20 in which the carriage stop 68 is connected to the second target 104. FIG. 5d depicts an embodiment of the connected carriage stop 68 in the first state 72. FIG. 5e depicts an embodiment of the connected carriage stop 68 in an embodiment of the second state 76 comprising the second position 76a. As depicted in FIG. 5e, the means for switching 88 optionally comprises a hinge 90. FIG. 5f depicts another embodiment of the connected carriage stop 68 in another embodiment of the second state 76 comprising the second position 76a. In embodiment depicted in FIG. 5f, the means for switching 88 retracts the impact portion 30h of the carriage stop 68 to switch from the first state 72 to the second state 76.

In one embodiment, the shock and launch apparatus 20 comprises an apparatus guide 96. The apparatus guide 96 is capable of collectively guiding the motion of the carriage guide 36 and the first and second carriages 24, 28. The embodiment of the shock and launch apparatus 20 depicted in FIG. 6 has one embodiment of the apparatus guide 96 which comprises at least one apparatus guide rod 98, e.g., two apparatus guide rods 98. The apparatus guide 96 can be used, for example, to provide a common velocity to the carriage guide 36 and the first and second carriages 24, 28. The shock and launch apparatus 20 comprises an interface 106 between the apparatus guide 96 and at least one other component of the shock and launch apparatus 20. In one embodiment, the interface 106 comprises an interface surface 108 which contacts at least one surface of the apparatus guide 96. In one embodiment, the interface 106 coincides with another component of the shock and launch apparatus 20. In the embodiment depicted in FIG. 6, the shock and launch apparatus 20 comprises the interface 106 which is between the apparatus guide 96 and the carriage guide 36, and which at least partially coincides with the second target 104.

Embodiments of the shock and launch apparatus 20 comprising the second target 104 are especially useful for providing a mechanical shock to a test object 112. For example, the embodiment of the shock and launch apparatus 20 depicted in FIG. 1 is capable of delivering the mechanical shock to the test object 112.

Figure 7A:
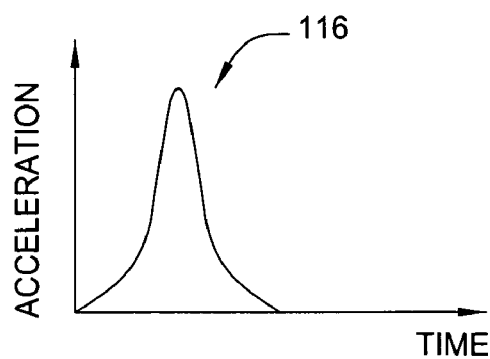
FIGS. 7a-c depict embodiments of a shock acceleration pulse which the shock and launch apparatus is capable of providing.
Figure 7B:
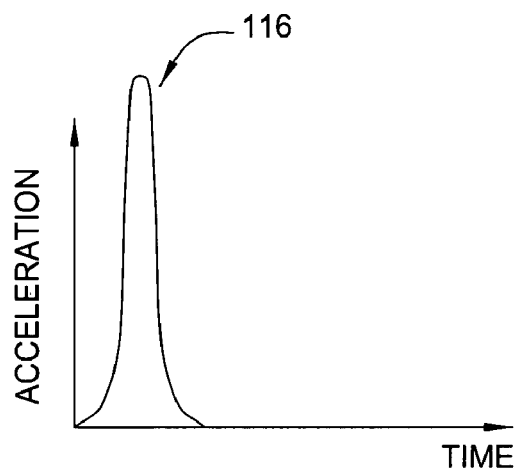
Figure 7C:
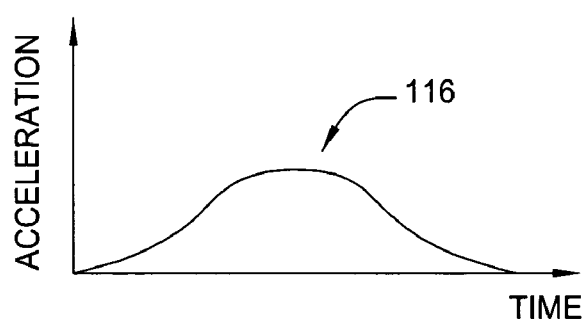

The mechanical shock is an acceleration applied to the test object 112. Equivalently, the shock can be characterized as a change in velocity of the test object 112. The shock comprises an acceleration magnitude as a function of time. In one embodiment, the shock and launch apparatus 20 delivers a shock acceleration which comprises a shock acceleration pulse 116. FIGS. 7a-c depict graphs having representations of embodiments of the shock acceleration pulse 116. In FIGS. 7a-c, the x-axis represents time, the y-axis represents acceleration magnitude, the curve represents the shock acceleration pulse 116, and the magnitude of the area under the curve represents the change in velocity imparted by the shock acceleration pulse 116 to the test object 112. Optionally, the shock and launch apparatus 20 delivers a shock acceleration which comprises an acceleration as a function of time having a form other than that of the pulse 116.

Figure 8:
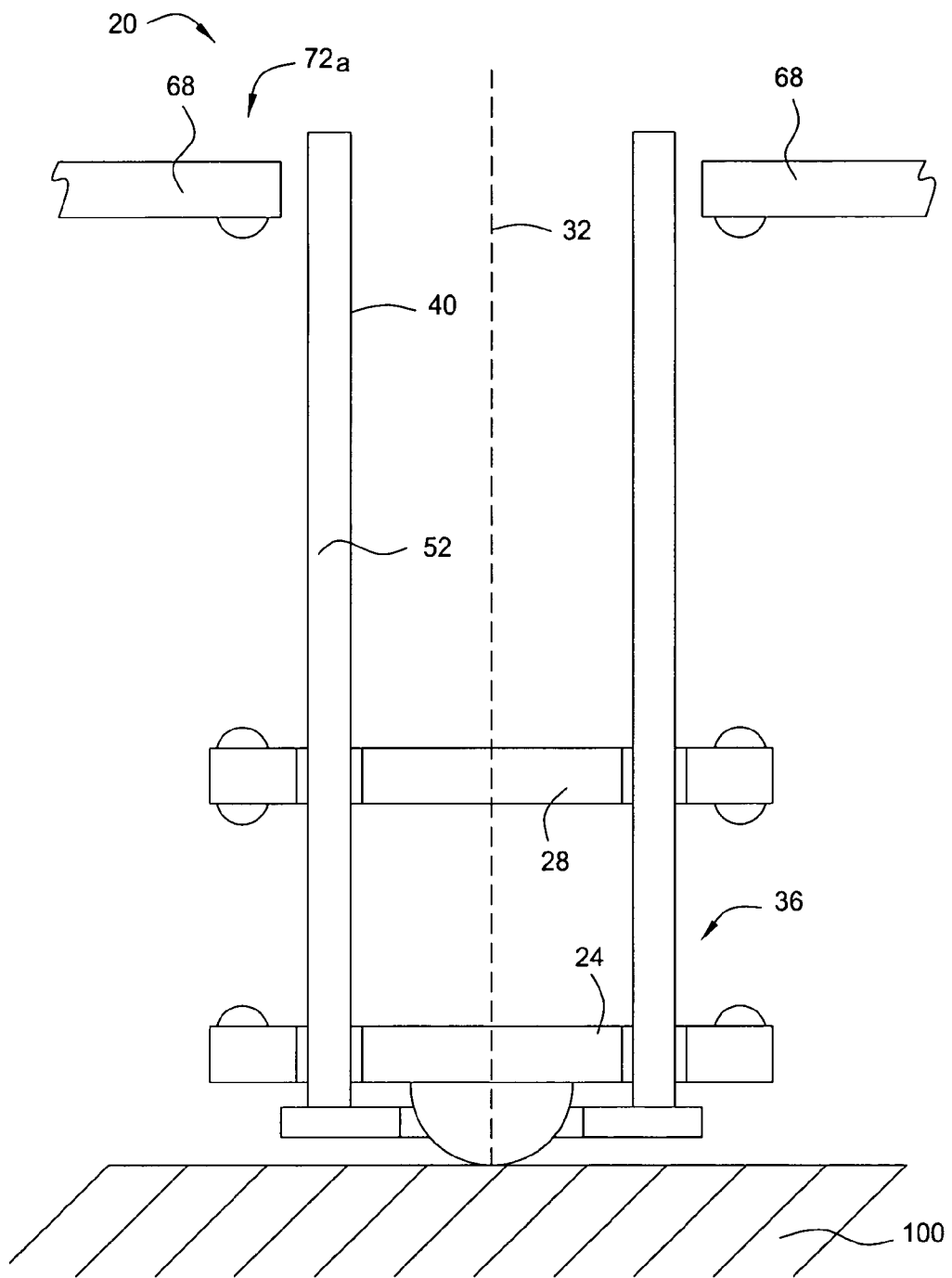
FIG. 8 depicts an embodiment of the shock and launch apparatus capable of launching an object.

Embodiments of the shock and launch apparatus 20 which do not comprise the second target 104 are especially useful for launching the test object 112. FIG. 8 depicts one embodiment of the shock and launch apparatus 20 which does not comprise the second target 104 and which is useful for launching the test object 112.

The test object 112 comprises any object which it is desirable to test or otherwise manipulate using the shock and launch apparatus 20. The test object 112 can comprise a variety of sizes, shapes and masses. In one embodiment, the test object 112 is relatively small and comprises, for example, a MEMs device. In one embodiment, the test object 112 is relatively large and comprises, for example, a space satellite. The test object 112 can be attached either permanently or temporarily to various components of the shock and launch apparatus 20. In one embodiment, the test object 112 is attached to the second target 104. In one embodiment, the test object 112 is attached to the second carriage 28. In one embodiment, the test object 112 coincides with the second carriage 28.

A method suitable for operating the shock and launch apparatus 20 comprises providing a velocity-reversing impact between the first carriage 24 and the first target 100. The velocity reversing impact provides a change in the direction of movement of the first carriage 24. The first and second carriages 24, 28 are provided with initial velocities $V_{1a}$ and $V_{2a}$, respectively, in a first direction $D_1$ towards the first target 100. In one embodiment, the first carriage 24, the second carriage 28, the carriage guide 36 and the carriage stop 68 are all provided with the same initial velocity magnitude in the direction $D_1$. The first carriage 24 impacts the first target 100 and reverses direction. After the velocity reversing impact, the first carriage 24 has a second velocity $V_{1b}$ in a second direction $D_2$ away from the first target 100 and towards the second carriage 28.

In the embodiment depicted in FIG. 1, the first direction $D_1$ is the downward direction and the second direction $D_2$ is the upward direction. However, in other embodiments the directions $D_1$ and $D_2$ are not necessarily downward and upward, respectively, but may be upward and downward, respectively, horizontal or any other direction which is toward the first target 100 from the first carriage 24 and toward the second carriage 28 from the first carriage 24, respectively. One advantage of embodiments in which the direction $D_1$ is the downward direction is that gravity may be used, at least in part, to provide the initial velocities $V_{1a}$ and $V_{2a}$.

The velocity magnitude $V_{1b}$ is related to the restitution $e_1$ of the impact between the first carriage 24 and the first target 100. The restitution e of an impact is a measure of the conservation of kinetic energy of objects involved in the impact. For example, a completely elastic impact, with e=1, has 100% restitution and completely conserves the kinetic energy of the involved objects. A completely inelastic impact, with e=0, has 0% restitution and does not conserve the kinetic energy of the involved objects. In one embodiment, the first target 100 is not moving and has a velocity magnitude which is zero. In this scenario, the relationship between $V_{1b}$ and $e_1$ is as follows: $V_{1b}=-e_1V_{1a}$. The restitution $e_1$ is related to the material and structural properties of the impact portion 30a of the first carriage 24 and the impact portion 30f of the first target 100. A restitution $e_1=1$, i.e. 100%, gives $V_{1b}=-V_{1a}$. Generally speaking, it is desirable for $e_1$ to be as high as possible.

The method comprises providing a plurality of velocity-amplifying impacts between the second carriage 28 and the first carriage 24 after the velocity-reversing impact between the first carriage 24 and the first target 100. After the velocity-reversing impact involving the first carriage 24, the first carriage 24 is moving at the velocity $V_{1b}$ in the direction $D_2$ towards the second carriage 28, and the second carriage 28 has been provided with an initial velocity magnitude $V_{2a}$ in the direction $D_1$ towards the first carriage 24. The first and second carriages 24, 28 impact each other to provide a velocity-amplifying impact to the second carriage 28. After the velocity-amplifying impact, the second carriage 28 has a second velocity $V_{2b}$ in the second direction $D_2$ towards the carriage stop 68 and the first carriage 24 has a third velocity $V_{1c}$ also in the second direction $D_2$.

The velocity magnitude $V_{2b}$ is related to the restitution $e_2$ of the impact between the first and second carriages 24, 28, and to the dynamics of the impact between the first and second carriages 24, 28, including the relative magnitudes of the fist and second masses $M_1$, $M_2$. The restitution $e_2$ is related to the material and structural properties of the impact portion 30b of the first carriage 24 and the impact portion 30c of the second carriage 28. Generally speaking, it is desirable for $e_2$ to be as high as possible. The second carriage 28 experiences both velocity reversal and velocity amplification as a result of the impact in part because the first mass $M_1$ of the first carriage 24 is greater than the second mass $M_2$ of the second carriage 28. For example, in a scenario in which $M_1/M_2 \approx \infty$, $V_{1a}=V_{2a}$, $e_1=1$, and $e_2=1$, after the impact both the first and second carriages 24, 28 move in the direction $D_2$, with the first carriage 24 having an approximately unchanged velocity $V_{1c} \approx V_{1b}$ and the second carriage 28 having a velocity $V_{2b} \approx -3V_{2a}$. Thus, in this scenario, the second carriage 28 experiences a change in velocity $\Delta V_2 \approx 4V_{2a}$. It is noted that although this scenario may contain idealized assumptions such as $M_1/M_2 \approx \infty$, $e_1=1$, and $e_2=1$, it nevertheless illustrates the principle of velocity amplification provided to the second carriage 28. Moreover, velocity amplification can also be achieved in non-idealized scenarios in which $M_1/M_2 \approx \infty$, $e_1=1$, and $e_2=1$ do not necessarily hold true. In one embodiment, a first level of velocity amplification performance can be achieved with $M_1/M_2>3$, and in another embodiment, a second level of velocity amplification performance can be achieved with $M_1/M_2>10$.

The method comprises providing a plurality of velocity-reversing impacts between the second carriage 28 and the carriage stop 68 in the first state 72. For example, after the first of the plurality of velocity-amplifying impacts between the first and second carriages 24, 28, the second carriage 28 is moving at the velocity magnitude $V_{2b}$ in the direction $D_2$ towards the carriage stop 68 in the first position 72a. The second carriage 28 impacts the carriage stop 68 in the first position 72a and is provided with a velocity-reversing impact. After the velocity reversing impact between the second carriage 28 and the carriage stop 68 in the first position 72a, the second carriage 28 is moving at the velocity magnitude $V_{2c}$ in the direction $D_1$ towards the first carriage 24.

The velocity magnitude $V_{2c}$ is related to the restitution $e_3$ of the impact between the second carriage 28 and the carriage stop 68. In one embodiment, the carriage stop 68 is not moving and has a velocity magnitude which is zero. In this scenario, the relationship between $V_{2c}$ and $e_3$ is as follows: $V_{2c}=-e_3V_{2b}$. The restitution $e_3$ is related to the impact portion 30d of the second carriage 28 and the impact portion 30h of the carriage stop 68 in the first state 72. Generally speaking, it is desirable for $e_3$ to be as high as possible.

After the velocity-reversing impact between the second carriage 28 and the carriage stop 68, the second carriage 28 is again moving in the direction $D_1$ towards the first carriage 24, which is still moving in the direction $D_2$ towards the second carriage 28. At this point, the second of the plurality of velocity-amplifying impacts between the first and second carriages 24, 28 occurs. After this second velocity-amplifying impact, the second carriage 28 is again headed in the direction $D_2$ towards the carriage stop 68 in the first position 72a and the second of the velocity-reversing impacts between the second carriage 28 and the carriage stop 68 occurs. In this manner, the process is repeated and the plurality of the velocity-amplifying impacts between the first carriage 24 and the second carriage 28, and the plurality of velocity-reversing impacts between the second carriage 28 and the carriage stop 68 in the first position 72a, are achieved. The overall velocity amplification provided to the second carriage 28 is cumulative over the plurality of velocity-amplifying impacts.

The method comprises switching the state of the carriage stop 68 from the first state 72 to the second state 76. The switching is based on the second carriage 28 reaching a desirable velocity or overall velocity amplification. In one embodiment, the method comprises determining at least one of: the position of the first carriage 24, the velocity of the first carriage 24, the velocity of the second carriage 28, the number of impacts that have occurred between the first and second carriages 24, 28, or the number of impacts that have occurred between the second carriage 28 and the carriage stop 68 in the first state 72; and the switching is in response to the determining step returning a certain result that indicates the second carriage 28 has or will reach the desired velocity.

In one embodiment, switching the carriage stop 68 to the second stage 76 comprises switching the carriage stop 68 to the second position 76a which allows the second carriage 28 to impact the second target 104. In one embodiment, switching the carriage stop 68 to the second stage 76 comprises switching the carriage stop 68 to the second position 76b which allows the second carriage 28 to impact the carriage stop in the second position 76b. In one embodiment, the test object 112 is attached to the second carriage 28 and the impact of the second carriage 28 with the second target 104, or the carriage stop 68 in the second position 76b, provides the shock acceleration to the test object 112. In one embodiment, the test object 112 is attached to the second target 104 or the carriage stop in the second position 76b, and the impact of the second carriage 28 with the second target 104, or the carriage stop 68 in the second position 76b, provides the test object 112 with an impact with the second carriage 28.

In one embodiment, the switching of the carriage stop 68 to the second position 76a allows the second carriage 28 to be launched from the shock and launch apparatus 20. For example, the shock and launch apparatus 20 can be used to launch satellites, projectiles, vehicles, etc.

In one embodiment, the method comprises moving the carriage stop 68 in the first state 72 towards the second carriage 28, i.e., in the direction $D_1$, while providing the plurality of velocity-reversing impacts between the second carriage 28 and the carriage stop 68 in the first state 72. In this embodiment, the plurality of velocity-reversing impacts may also become velocity-amplifying impacts between the second carriage 28 and the carriage stop 68 in the first state 72.

The properties of the shock acceleration produced by the shock and launch apparatus 20 can be selected by selecting the material and structural properties of the first and second carriages 24, 28, first and second targets 100, 104, and the impact portions 30 thereof. In one embodiment, the properties of particular impact portions 30 are selected to shape the shock acceleration pulse 116 experienced by the second carriage 28 and the test object 112. For example, FIG. 7a depicts one embodiment of the shock acceleration pulse 116 which has a representative height and width. FIG. 7b depicts another embodiment of the shock acceleration pulse 116 having a height which is increased and a width which is decreased, i.e., an increased peak acceleration magnitude and a decreased duration of the pulse 116. FIG. 7c depicts another embodiment of the shock acceleration pulse 116 having a height which is decreased and a width which is increased, i.e., a decreased peak acceleration magnitude and an increased duration of the pulse 116. Generally speaking, it is possible to proportionately increase the height and decrease the width of the pulse 116, or decrease the height and increase the width, while maintaining the same area under the pulse 116, i.e. the same change in velocity imparted by the pulse 116.

In one embodiment, to provide an impact having a relatively increased acceleration magnitude, at least one of the material or structure of the impact portion 30 is selected to provide an elastic response having a relatively short time constant which enables the impact to produce a shock acceleration having a relatively higher magnitude and shorter duration. Examples of materials that are suitable for producing these relatively short time constant elastic impacts include impact portions 30 comprising relatively harder elastic materials such as, for example, metals, hard plastics, quartz, diamonds, etc. In one embodiment, it is desirable for the impact involving the second carriage 28 and the second target 104, or the second carriage 28 and the carriage stop 68 in the second state 76b, and also the test object 112, to experience acceleration as high in magnitude as possible. Thus, in one embodiment, the materials and structures described in this paragraph are used especially for the impact portions 30e, 30g, 30i of the second carriage 28, second target 104 and carriage stop 68 in the second state 76b which impact each other.

In one embodiment, to provide an impact having a relatively decreased acceleration magnitude, at least one of the material or structure of the impact portion 30 is selected to provide an elastic response having a relatively longer time constant which enables the impact to produce a shock acceleration having a relatively lower magnitude and longer duration. Examples of materials that are suitable for producing these relatively longer time constant elastic impacts include impact portions 30 comprising relatively softer elastic materials such as, for example, elastomers, foams, rubber, etc. In one embodiment, it is not necessary for the impacts not involving the second target 104 or the carriage stop 68 in the second state 76b to experience accelerations as high in magnitude as possible, and thus the emphasis can instead be placed on achieving as high a restitution as possible. Thus, in one embodiment, the materials and structures described in this paragraph are used for the impact portions 30a, 30b, 30c, 30d, 30h not involved in the impact involving the second target 104 or the carriage stop 68 in the second state 76b.

In one embodiment, the first and second carriages 24, 28 each in part comprise a plate. The size, thickness and material of the plates are selected to provide the predetermined mass for each of the first and second carriages 24, 28. In one embodiment, the first and second carriages 24, 28 are each at least partially hollow and have internal structures which are selected to in part determine the stiffness of their impact portions 30. Also, different hollowing of the first and second carriages 24, 28 can be used to achieve the greater mass of the first carriage 24 relative to the second carriage 28.

In one embodiment, the impact portion 30 comprises at least one of: a protrusion 31 or a curved surface 33. The impact portion 30 comprising the protrusion 31 or curved surface 33 provides desirable propagation characteristics of the shock acceleration through the first and second carriages 24, 28 and first and second targets 100, 104, contributes to shaping the shock acceleration pulse 116, and is used in part to increase the restitution of an impact. In one embodiment, for example as depicted in FIG. 1, each of the first and second carriages 24, 28 has impact portions 30 comprising a hemispherical protrusion 31 from the plate. In one embodiment, the first and second carriages 24, 28 are constructed such that different hemispherical protrusions 31 are interchangeable in the first and second carriages 24, 28 to vary the shock acceleration properties of an impact, and determine the overall operating characteristics of the shock and launch apparatus 20.

In one embodiment, the carriage guide 36 comprises an end stop 38 which constrains the movement of the first and second carriages 24, 28. For example, in conjunction with the second target 104, the end stop 38 constrains the movement of the first and second carriages 24, 28 from leaving the carriage guide 36 and the path 32 associated therewith. The end stop 38 comprises an aperture 39 to allow the impact portion 30 of the first carriage 24 to impact the first target 100. Optionally, the end stop 38 comprises a means 50 to allow a gentle impact between the end stop 38 and the first target 100, such as for example a spring or padding.

Figure 9A:
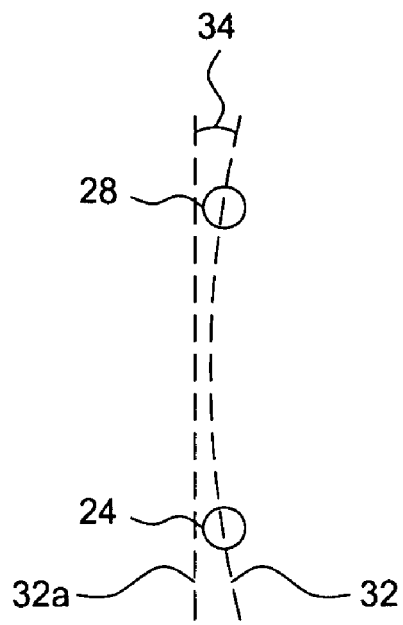
FIGS. 9a-b depict embodiments of a substantially linear path of movement associated with the shock and launch apparatus.
Figure 9B:
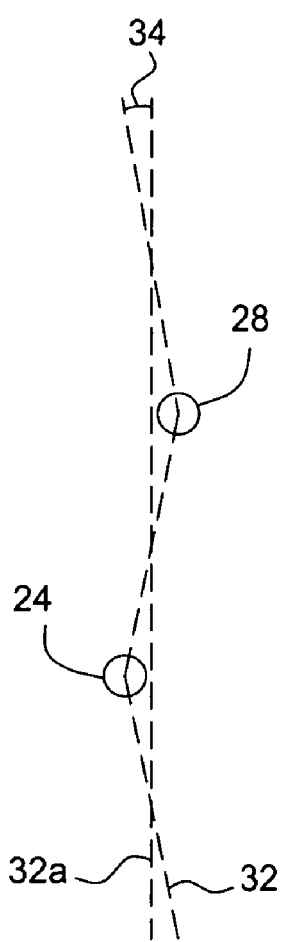

The substantially linear path 32 may deviate from linearity by at most a predetermined amount. In one embodiment, the substantially linear path 32 comprises a purely linear path 32a. In one embodiment, the substantially linear path 32 deviates from a purely linear path 32a as measured by an angle 34 between the substantially linear path 32 and the purely linear path 32a, the angle 34 being no greater than about 15°. For example, FIGS. 9a,b depict embodiments of the substantially linear path 32 which deviate from the purely linear path 32a by the angle 34 no greater than about 15°. Specifically, FIG. 9a depicts an embodiment of the path 32 having a curvature which falls within the predetermined angular deviation, and FIG. 4b depicts an embodiment of the path 32 having points offset from the purely linear path 32a such that the path 32 connecting the points falls within the predetermined angular deviation.

In one embodiment of the shock and launch apparatus 20, it is desirable to have relatively high restitution impacts in order to efficiently utilize the kinetic energy of all of the moving objects, including the first and second carriages 24, 28, and the shock and launch apparatus 20 enables each of the plurality of impacts to have an associated restitution e wherein $e \geq 0.5$.

In one embodiment, the shock and launch apparatus 20 comprises at least one spacer 80 which provides a predetermined separation distance between the first and second carriages 24, 28. The spacer 80 separates the first and second carriages 24, 28 to maintain the desired temporal order of impacts during operation of the shock and launch apparatus 20. Namely, the spacer 80 separates the first and second carriages 24, 28, and prevents an impact between the first and second carriages 24, 28, until after the velocity-reversing impact between the first carriage 24 and the first target 100.

The spacer 80 may comprise any suitable apparatus or means to create the desired predetermined separation distance between the first and second carriages 24, 28 until after the impact between the first carriage 24 and the first target 100. In one embodiment, the spacer 80 suspends the first and second carriages 24, 28 from another component such as, for example, the second target 104 or the carriage guide 36. For example, in one embodiment, the spacer 80 comprises a string 80a which is attached to the second target 104 and passes through the first and second carriages 24, 28 to suspend them from the second target 104. Optionally, the arrangement of the string can be selected to provide enough freedom of movement of the first and second carriages 24, 28, to allow all of the impacts involving the first and second carriages 24, 28. Optionally, the strength of the string 80a can be selected such that it breaks at an appropriate moment to allow the proper order of impacts. In one embodiment, the shock and launch apparatus 20 comprises a plurality of spacers 80 which independently position the first and second carriages 24, 28. In one embodiment, the spacer 80 has an obstruction after it passes through each of the first and second carriages 24, 28, thereby suspending each at a predetermined distance from each other and the second target 104.

In one embodiment, the spacer 80 comprises at least one retractable arm which holds the first and second carriages 24, 28 in an initial position and then retracts to release the first and second carriages 24, 28 at an appropriate moment.

In one embodiment, the spacer 80 comprises a spring 80b or other compressible object between the first and second carriages 24, 28. The compression characteristics, e.g., the spring constant, of the spring 80b are selected such that it maintains suitable separation between the first and second carriages 24, 28 in a first scenario, e.g., at rest or traveling at a first velocity, and compresses in a second scenario, e.g., under a second set of velocities or the presence of an acceleration differential, thus allowing the first and second carriages 24, 28 to impact each other at appropriate moments.

In one embodiment, instead of a separate spacer 80, at least one of the first and second carriages 24, 28 comprises an integral structure or portion which achieves a similar function. For example, the integral structure or portion may be selectively compressible.

In one embodiment, the shock and launch apparatus 20 comprises a propelling means 120 which provides the predetermined initial velocity to the first and second carriages 24, 28 and optionally other components such as the carriage guide 36. The propelling means 120 may comprise a variety of forms. FIG. 6 depicts one embodiment of the shock and launch apparatus 20 comprising the propelling means 120. In the embodiment depicted, the propelling means 120 comprises a spring 122. The spring 122 is compressed and calibrated to provide the predetermined initial velocity to the first and second carriages 24, 28.

The spring 122 is not the only possible propelling means 120, however. In another embodiment, the propelling means 120 comprises a ballistic means, such as, e.g., a canon. In one embodiment, the propelling means 120 comprises a gas source. For example, in one embodiment a pressurized gas source is focused about the first and second carriages 24, 28 to provide the predetermined initial velocities. The gas source also optionally comprises a heated gas. In one embodiment, the propelling means 120 comprises a magnetic propelling means having a magnet comprising at least one of: a permanent magnet, an electromagnet, or a superconducting magnet. The magnetic propelling means is arranged to provide a magnetic field about at least one of the first and second carriages 24, 28.

In one embodiment, the propelling means 120 is internal to at least one of the first and second carriages 24, 28. For example, in some embodiments, any of the propelling means 120 discussed above may be entirely or partially internal to at least one of the first and second carriages 24, 28 and arranged to provide a force from the at least one of the first and second carriages 24, 28 to the environment about the at least one of the first and second carriages 24, 28 to accelerate first and second carriages 24, 28 to the predetermined initial velocity.

Embodiments of the shock and launch apparatus 20 enable the plurality velocity-amplifying impacts which enable a relatively high acceleration to be provided. One advantage of the present invention over other methods and apparatuses is that it enables a high acceleration in a relatively contained and safe apparatus. The plurality of velocity-amplifying impacts enabled by the present invention may be described, from one perspective, as spatially folded. That is, the shock and launch apparatus 20 achieves an acceleration magnitude that would require the test object 112 be dropped from an impractically large height in a drop testing method or apparatus to achieve comparable acceleration magnitudes. The shock and launch apparatus 20 of the present invention instead achieves the same result in a much smaller space, and thus could be considered to be spatially folded in comparison to the larger space required by drop testing. Similarly, to achieve comparable acceleration magnitudes by ballistic methods would be undesirably dangerous and expensive.

Although described in the context of the shock and launch apparatus 20, the methods described herein have application in other contexts and in association with other apparatuses.

While the foregoing is directed to embodiments of the present invention, other and further embodiments of the invention may be devised without departing from the basic scope thereof, and the scope thereof is determined by the claims that follow. Various embodiments presented herein, or portions thereof, may be combined to create further embodiments. Furthermore, terms such as top, side, bottom, front, back, and the like are relative or positional terms and are used with respect to the exemplary embodiments illustrated in the figures, and as such these terms may be interchangeable.

The invention claimed is:

1. A method, comprising:
providing a velocity-reversing impact to a first carriage;
providing a plurality of velocity-amplifying impacts between a second carriage and the first carriage after the velocity-reversing impact to the first carriage, wherein the first carriage has a mass $m_1$ greater than the mass $m_2$ of the second carriage;
providing a plurality of velocity-reversing impacts between the second carriage and a carriage stop in a first position; and
changing the position of the carriage stop to a second position.

2. The method of claim 1, wherein $m_1$ is greater than $3 m_2$.

3. The method of claim 1, wherein the providing the velocity-reversing impact to the first carriage comprises:
providing an impact between the first carriage and a stationary object.

4. The method of claim 1, comprising:
providing the first and second carriages with an initial velocity; and
wherein the providing the plurality of velocity-amplifying impacts between the second carriage and the first carriage comprises selecting the number of velocity-amplifying impacts between the second carriage and the first carriage to determine the finally amplified velocity of the second carriage.

5. The method of claim 1, wherein the first and second positions of the carriage stop are stationary positions.

6. The method of claim 1, comprising providing a shock-acceleration-providing impact between the second carriage and a target, wherein the shock-acceleration-providing impact is provided after the providing of the plurality of velocity-amplifying impacts between the first and second carriages.

7. The method of claim 1, the changing the position of the carriage stop comprises detecting a predetermined number of the velocity-reversing impacts between the second carriage and the carriage stop.

8. The method of claim 1, comprising:
guiding the motion of the first and second carriages along a substantially linear path.

9. The method of claim 1, comprising:
providing a first impact portion of the first carriage and a second impact portion of the second carriage, wherein the characteristics of the first and second impact portions are selected to give a restitution for each of the plurality of velocity-amplifying impacts between the first and second carriages of greater than 50%; and
providing a third impact portion of the second carriage and a fourth impact portion of the second target, wherein the characteristics of the third and fourth impact portions are selected to determine the properties of a shock acceleration pulse provided by the shock and launch apparatus.

10. A shock and launch apparatus, comprising:
a first carriage and a second carriage adapted to move along a carriage guide, wherein the first carriage has a mass $m_1$ greater than a mass $m_2$ of the second carriage;
the carriage guide, associated with a substantially linear path of movement o the first and second carriages; and
a carriage stop, capable of being positioned at a first position and a second position, wherein the carriage stop in the first position is at least partially in the path of movement of the second carriage.

11. The shock and launch apparatus of claim 10, wherein the carriage stop in the second position is not in the path of movement of the second carriage, the shock and launch apparatus comprising:
a target fixedly attached to the carriage guide,
wherein the target is positioned so that the second carriage is capable of hitting the target as it moves in one direction along the carriage guide when the carriage stop is in the second position, and
wherein the target comprises a first impact portion and the second carriage comprises a second impact portion, and the characteristics of the first and second impact portions are selected to influence the shape of a shock experienced by the second carriage during an impact between the target and the second carriage, and wherein the characteristics include at least one of: the material properties of the first and second impact portions, or the structural properties of the first and second impact portions.

12. The apparatus of claim 10, comprising:
a detector to detect a number of impacts between the first and second carriages.

13. The apparatus of claim 12, comprising:
a means for switching the position the carriage stop between the first and second positions, wherein the means for switching is responsive to the detector to determine at which of the first and second positions to position the carriage stop.

14. The apparatus of claim 10, wherein the first carriage comprises a first impact portion and the second carriage comprises a second impact portion, wherein the characteristics of the first and second impact portions are selected to give a restitution for an impact between the first and second carriages of greater than 50%, wherein the characteristics include at least one of: the material properties of the first and second impact portions, or the structural properties of the first and second impact portions.

15. The apparatus of claim 10, wherein $m_1$ is greater than $3 m_2$.

16. The apparatus of claim 10, comprising:

an apparatus guide to collectively guide the motion of the carriage guide, the first and second carriages and the carriage stop.

17. An apparatus, comprising:

means for providing a velocity-reversing impact to a first carriage;

means for providing a plurality of velocity-amplifying impacts between a second carriage and the first carriage, wherein the first carriage has a mass $m_1$ greater than the mass $m_2$ of the second carriage;

means for providing a plurality of velocity-reversing impacts between the second carriage and a carriage stop in a first position; and means for switching the position of the carriage stop to a second position.

18. The apparatus of claim 17, comprising:

means for providing an impact between the first carriage and a stationary target.

19. The apparatus of claim 17, comprising:

means for providing the first and second carriages with an initial velocity.

20. The apparatus of claim 17, comprising:

means for guiding the motion of the first and second carriages along a substantially linear path.

* * * * *